United States Patent [19]
Sullivan et al.

[11] Patent Number: 5,785,956
[45] Date of Patent: Jul. 28, 1998

[54] DUAL COMPONENT DENTIFRICE COMPOSITION FOR DENTAL FLUORIDATION

[75] Inventors: Richard J. Sullivan, Edison; Abdul Gaffar, Princeton, both of N.J.

[73] Assignee: Colgate Palmolive Company, New York, N.Y.

[21] Appl. No.: 664,226

[22] Filed: Jun. 7, 1996

[51] Int. Cl.$^6$ .................. A61K 7/16; A61K 7/18
[52] U.S. Cl. ........................ 424/52; 414/49
[58] Field of Search ..................... 424/49–88

[56] References Cited

U.S. PATENT DOCUMENTS

| | | | |
|---|---|---|---|
| 3,175,731 | 3/1965 | Ellman | 222/94 |
| 3,980,767 | 9/1976 | Chown et al. | 424/52 |
| 4,098,435 | 7/1978 | Weyn | 222/94 |
| 4,203,966 | 5/1980 | Faunce | 424/52 |
| 4,358,437 | 11/1982 | Duke | 424/52 |
| 4,411,876 | 10/1983 | Sherif | 423/311 |
| 4,425,322 | 1/1984 | Harvey, II et al. | 424/52 |
| 4,425,324 | 1/1984 | Harvey, I et al | 424/52 |
| 4,592,487 | 6/1986 | Simon et al. | 222/94 |
| 4,814,160 | 3/1989 | Carter et al. | 424/52 |
| 5,108,728 | 4/1992 | Rau et al. | 423/309 |
| 5,145,668 | 9/1992 | Chow et al. | 424/52 |
| 5,603,922 | 2/1997 | Winston et al. | 424/52 |
| 5,605,675 | 2/1997 | Usen et al. | 424/52 |

OTHER PUBLICATIONS

Abstracts of Han et al C.A. 122: 1965717 CN 1093668A (Oct. 19, 1994).
Wang et al C.A. 115: 2630957 CN 1044224A (Aug. 1, 1991).

*Primary Examiner*—Shep K. Rose
*Attorney, Agent, or Firm*—Paul Shapiro

[57] ABSTRACT

A dual component dentifrice composition in which the first component is a stable, semi-solid, extrudable dentifrice composition containing a fluoride ion releasable compound in which calcium ion is absent and the second component is a semi-solid, extrudable dentifrice composition containing a dicalcium phosphate abrasive having a magnesium ion content less than about 0.5% by weight wherein increased fluoride uptake is achieved when the components are mixed upon application to dental tissue.

14 Claims, No Drawings

DUAL COMPONENT DENTIFRICE COMPOSITION FOR DENTAL FLUORIDATION

BACKGROUND OF THE INVENTION

1. Field of the Invention

This invention is directed to a dentifrice composition containing fluoride releasing compounds and more particularly to a dual component dentifrice composition for fluoridating teeth providing enhanced fluoride deposition.

2. The Prior Art

It has long been known to include fluoride releasing compounds in dentifrices as anticaries agents, and it has been established that these compounds are effective to reduce the incidence of dental caries. Fluoride compounds which are conventionally used are sodium fluoride, sodium monofluorophosphate and stannous fluoride. The fluoride compounds are effective mainly due to the fluoride ions which improve the acid resistance of tooth enamel and accelerate recalcification or remineralization of decayed teeth in their early stage when the demineralization has proceeded only slightly. The effect of improving the acid resistance of the enamel is believed to be due to the fact that the fluoride ions are incorporated into a crystal lattice of hydroxyapatite which is the main constituent of tooth enamel or, in other words, fluoride ions partially fluoridate hydroxyapatite and simultaneously repair the lattice irregularities.

The effectiveness of fluoride treatment is dependent upon the amount of fluoride ion which is available for deposition on the enamel being treated. It is, therefore, desirable to formulate dentifrice compositions which provide maximum fluoride ion availability in brushing solutions formed using the dentifrice.

It is known to the art, e.g., U.S. Pat. No. 5,045,305, that an effective way of depositing fluoride on teeth is to use a two-component composition to precipitate calcium fluoride on teeth in which one component contains $CaCl_2$ and the other contains fluoride ions in the form of NaF, the separate components being admixed immediately prior to introduction in the mouth, to effect precipitation of $CaF_2$. Investigation of the two-component NaF—$CaCl_2$ system, demonstrated that it is ineffective in producing high levels of fluoride deposition.

U.S. Pat. No. 5,145,668 discloses a method of fluoridating teeth wherein there is mixed in the mouth a first component comprising a soluble calcium salt such as $CaCl_2$ contained in a non-reactive vehicle and a second component containing a hydrolyzable complex fluoride compound such as sodium fluorosilicate ($Na_2SiF_6$) contained in a non-reactive vehicle, the mixing of the components resulting in hydrolysis of the complex fluoride compound and precipitation of calcium fluoride and its deposition on tooth surfaces.

One disadvantage of the two-component fluoride deposition system described in U.S. 5,145,668 is that it requires the use of a complex fluoride compound that has a specific hydrolytic property. The compounds known to be suitable for this purpose include the salts of fluorosilisic acid ($H_2SiF_6$) and fluorostannic acid ($H_2SnF_6$). Because none of the suitable complex fluoride salts are currently approved by the US Food and Drug Administration for use in rinses, dentifrices, and other oral health care products, a great investment of expense and effort will be required to demonstrate safety in addition to efficacy before these fluoride compounds may be used clinically.

A two component dentifrice system is disclosed in U.S. Pat. No. 4,098,435 which utilizes FDA approved fluoride salts and FDA approved calcium containing abrasives wherein one component of the system contains an alkali metal fluoride containing salt such as sodium fluoride or sodium monofluorophosphate for fluoride treatment of teeth and the other contains a calcium containing abrasive such as dicalcium phosphate, tricalcium phosphate or calcium carbonate, for tooth cleaning, the components being physically separated from each other in a dispensing container from which they are dispensable together through a closable opening in response to pressure applied to the container.

Attempts to utilize the two component dentifrice disclosed in U.S. Pat. No. 4,098,435 to produce high levels of fluoride deposition do not immediately achieve theoretical maximum fluoride availability as precipitated $CaF_2$ when the two components are mixed during brushing of the teeth.

Thus, there is a need in the art to formulate a semi-solid two component fluoride deposition dentifrice system utilizing FDA approved fluoride salts and calcium abrasives wherein optimum uptake of fluoride on dental tissue is accomplished when the fluoride containing component is mixed with the calcium containing abrasive dentifrice component on application to tooth surfaces.

SUMMARY OF THE INVENTION

In accordance with the present invention there is provided a dentifrice for fluoridating teeth utilizing two separate semi-solid components such as pastes or gels which contain fluoride salt and calcium ion containing abrasive ingredients which are reactive when mixed together upon application to teeth, the first component being a stable, semi-solid dentifrice composition containing a fluoride ion releasing salt in a vehicle in which the ingredients thereof are non-reactive with the fluoride salt, the vehicle being free of calcium ion containing compounds, the second component comprised of a vehicle containing a hydrated dicalcium phosphate abrasive containing less than about 0.5% by weight magnesium ion based on the weight of the dicalcium phosphate, wherein the individual dentifrice components are substantially rhelogically equivalent so that the dual components, when dispensed simultaneously, are dispensed synchronously and uniformly whereby the ingredients are at the proper reactant ratio to provide maximum fluoride availability upon mixing of the components during application to the teeth as by brushing.

DESCRIPTION OF THE PREFERRED EMBODIMENTS

The vehicle used to prepare the individual components of the dual component dentifrice composition of the present invention includes water and a suitable humectant such as glycerin, sorbitol, propylene glycol, polyethylene glycol, or any suitable mixture thereof. Glycerin or a mixture of glycerin and sorbitol is preferred as the humectant in the practice of the present invention. The humectant comprises about 20 to about 70% by weight of the dentifrice component and preferably about 20 to about 65% by weight. Water may be included in the vehicle used to prepare the dentifrice components at a concentration of about 2 to about 40% by weight of the composition and preferably about 2 to about 30% by weight.

The amount of vehicle used in the practice of the invention is preferably sufficient to impart to the dentifrice component the pasty consistency, body and non-tacky nature which is characteristic of conventional toothpastes or gels.

The rheological properties of the dentifrice components expressed on a numerical basis, as the viscosity of each of the dentifrice components, based on the Brookfield system, range from about 15 to about 50 Brookfield Units at 230° C. At a viscosity above about 50 Brookfield Units the viscosity of the dentifrice components is too high to meet the flow requirements of commercial filling operations. At a viscosity below about 15 Brookfield Units the fluidity of the dentifrice components creates miscibility problems between the components during commercial filling operations. As used herein, viscosity expressed as Brookfield Units is measured with a Brookfield Digital Viscometer Model DVII using spindle number 95 at 5 revolutions per minute at 230° C.

By the term "substantially equivalent rheologies" or "substantial rheological equivalence" is meant that the individual components of the two component dentifrice of the present invention have sufficiently similar viscosities so that synchronous dispensing as well as measured interaction is effected between the fluoride salt and calcium containing abrasive ingredients of the components when the components are dispensed together and mixed in the oral cavity. The concentration of the fluoride salt and calcium containing abrasive ingredients present in the individual dentifrice components is controlled so that maximum interaction of these ingredients will occur when the components are coextruded at a volume ratio of 0.9:1 to 1:0.9 and preferably 1:1.

Surfactants are used in the preparation of dentifrice components of the present invention to aid in the thorough dispersion of the dentifrice components throughout the oral cavity when applied thereto as well as to improve the cosmetic acceptability and detersive and foaming properties of the combined components. Among the surfactants useful in the practice of the present invention are salts of the higher alkyl sulfates, such as sodium lauryl sulfate or other suitable alkyl sulfate having 8 to 18 carbon atoms in the alkyl group; sodium lauryl sulfoacetate, salts of sulfonated monoglycerides of higher fatty acids, such as sodium coconut monoglyceride sulfonate or other suitable sulfonated monoglycerides of a fatty acids of 10 to 18 carbon atoms; salts of amides of higher fatty acid, e.g., 12 to 16 carbon atom acids, with lower aliphatic amino acids, such as sodium-N-methyl-N-palmitoyl tauride, sodium N-lauroyl-, N-myristoyl- and N-palmitoyl sarcosinates; salts of the esters of such fatty acids with isotonic acid or with glycerol monosulfate, such as the sodium salt of monosulfated monoglyceride of hydrogenated coconut oil fatty acids; salts of olefin sulfonates, e.g. alkene sulfonates or alkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt may be sodium (which is preferred), potassium or mono-, di or triethanol amine.

The surfactant is included in the dentifrice vehicle of the individual components of the present invention at a concentration of about 0.5 to about 3.0% by weight and preferably about 1.0 to about 2.0% by weight.

Thickeners such as natural and synthetic gums and colloids may also be incorporated in the dentifrice components of the present invention, examples of which include iota carrageenan, xanthan gum, carboxymethyl cellulose, sodium carboxymethyl cellulose, starch, polyvinylpyrrolidone, amorphous silica, hydroxyethylpropylcellulose, hydroxybutyl methyl cellulose, hydroxypropyl methyl cellulose and hydroxyethyl cellulose. The thickener may be incorporated in the dentifrice components of the present invention at a concentration of about 0.2 to about 8% by weight and preferably about 0.3 to about 6.0% by weight.

The first component of the dual component dentifrice composition of the present invention contains a water soluble fluoride releasable salt such as an alkali metal fluoride such as NaF, KF, sodium monofluorophosphate or $SnF_2$. The preferred fluoride salt for the purposes of this invention is NaF.

The fluoride salt is incorporated in the first component of the dentifrice composition of the present invention at a concentration of about 0.1 to about 1% by weight, and preferably at about 0.25 to about 0.5% by weight. At these preferred concentrations, about 750 ppm to about 1500 ppm, fluoride ion will be available to teeth when the combined first and second components of the dentifrice composition are admixed when applied to the teeth.

The second component of the dentifrice composition of the present invention contains a hydrated dicalcium phosphate abrasive and preferably a dicalcium phosphate dihydrate abrasive and most preferably a dicalcium orthophosphate dihydrate. The hydrated calcium diphosphate abrasive is incorporated in the second component of the dentifrice composition of the present invention at a concentration of about 30 to about 55% by weight and preferably at about 40 to about 50% by weight of the component.

It is known to the art (U.S. Pat. No. 4,244,931) to stabilize a dicalcium orthophosphate dental abrasive against spontaneous hydrolysis and/or decomposition with a small amount of tetrasodium pyrophosphate or with trimagnesium orthophosphate. Dicalcium phosphate dihydrate dental abrasive presently available commercially is stabilized against spontaneous hydrolysis and/or decomposition with a small amount of a combination of tetrasodium pyrophosphate and trimagnesium phosphate, the magnesium ion content of which ranges from about 0.5 to about 0.8% by weight of the calcium abrasive and the pyrophosphate content ranges from about 0.1 to about 0.4% by weight of the abrasive.

It is a critical feature of the present invention that the hydrated dicalcium phosphate abrasive contain less than about 0.5% by weight of magnesium ion, for it has been unexpectedly discovered that at these lesser levels optimum fluoride deposition on tooth surfaces is obtained when the calcium abrasive dentifrice component is admixed with the fluoride containing component in the oral cavity as by brushing tooth surfaces with the combined dentifrice components.

The dicalcium phosphate abrasive is contained in a vehicle formulated to have a composition similar to the vehicle of the first dentifrice component, so that two components will be of substantially equivalent rheologies, which will permit them to be synchronously coextrudable. In order to maintain that the physical characteristics of the second component have Theological properties substantially equivalent to the first component, the vehicle composition of the second component, specifically the humectant and thickener content, is adjusted to accommodate the inclusion of the dicalcium phosphate abrasive. The abrasive is included in the second dentifrice component at a concentration of about 30 to about 50% by weight and preferably at a concentration of about 40 to about 50% by weight. At these abrasive levels, the humectant concentration ranges from about 15 to about 35% by weight and preferably about 20 to about 30% by weight. In such abrasive containing second component, as the inclusion of the abrasive has a thickening effect, a non-reactive abrasive such as silica may be included in the first component at a concentration of about 10 to about 25% by weight and preferably about 15 to about 20% by weight as well as additional thickening agents such as amorphous silica at about 3 to about 10% by weight.

Salts having anti-tartar efficacy including water soluble salts such as dialkali or tetra-alkali metal pyrophosphate salts such as $Na_4P_2O_7$, $K_4P_2O_7$, $Na_2K_2P_2O_7$, $Na_2H_2P_2O_7$ and $K_2H_2P_2O_7$, long chain polyphosphate such as sodium hexametaphosphate and cyclic phosphates such as sodium trimetaphosphate as well as alkali metal tripolyphosphates such as sodium tripolyphosphate and potassium tripolyphosphate may be incorporated in the calcium abrasive containing component of the present invention preferably at a concentration of about 0.5 to about 5.0% by weight and preferably about 1.0 to about 3% by weight.

A striped dentifrice product is obtained in accordance with the practice of the present invention wherein colorants of contrasting colors are incorporated in each of the dentifrice components used in the practice of the present invention, the colorants being pharmacologically and physiologically non-toxic when used in the suggested amounts. Colorants used in the practice of the present invention include both pigments and dyes.

Pigments used in the practice of the present invention include non-toxic, water insoluble inorganic pigments such as titanium dioxide and chromium oxide greens, ultramarine blues and pinks and ferric oxides as well as water insoluble dye lakes prepared by extending calcium or aluminum salts of FD&C dyes on alumina such as FD&C Green #1 lake, FD&C Blue #2 lake, FD&C R&D #30 lake and FD&C # Yellow 15 lake. The pigments have a particle size in the range of 5–1000 microns, preferably 250–500 microns, and are present at a concentration of 0.5 to 3% by weight.

The dyes used in the practice of the present invention are distributed uniformly throughout the dentifrice component and are generally food color additives presently certified under the Food Drug & Cosmetic Act for use in food and ingested drugs, including dyes such as FD&C Red No. 3 (sodium salt of tetraiodofluorescein), FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4- hydroxy-2-sulfoniumphenyl)-methylene}-[1-(N-ethyl-N-p-sulfobenzyl)-Δ-3,5-cyclohexadienimine], FD&C Blue No. 1 (disodium salt of dibenzyldiethyl-diaminotriphenylcarbinol trisulfonic acid anhydrite), FD&C Blue No. 2(sodium salt of disulfonic acid of indigotin) and mixtures thereof in various proportions. The concentration of the dye for the most effective result in the present invention is present in the dentifrice composition in an amount from about 0.0005 percent to about 2 percent by weight.

It is preferred that the colorant included in one of the dentifrice components be a pigment such as $TiO_2$ and that colorant distributed throughout the body of the other dentifrice component be a dye and the dye be of a different color than the pigment included in the first dentifrice component.

Any suitable flavoring or sweetening material may also be employed. Examples of suitable flavoring constituents are flavoring oils, e.g., oils of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, sodium cyclamate, perillartine, and sodium saccharin. Suitably, flavor and sweetening agents may together comprise from 0.01% to 5% or more of the preparations.

Various other materials may be incorporated into the dentifrice components of this invention. Non-limiting examples thereof include preservatives, silicones and chlorophyll compounds, antibacterial agents such as chlorohexidene, halogenated diphenyl ethers such as triclosan, desensitizing agents such as potassium nitrate and potassium citrate and mixtures thereof. These adjuvants are incorporated in the dentifrice components in amounts which do not substantially adversely affect the properties and characteristics desired, and are selected and used in proper amounts, depending upon the particular type of dentifrice component involved.

To prepare the individual dentifrice component of the present invention, water, humectants, e.g. glycerin, sorbitol, polyethylene glycol and sweetener are dispersed in a conventional mixer until the mixture becomes a homogeneous gel phase. Into the gel phase are added the fluoride salt or dicalcium phosphate abrasive. These ingredients are mixed until a homogeneous phase is obtained. Thereafter the thickener, flavor and surfactant ingredients are added and the ingredients mixed at high speed under vacuum of about 20–100 mm Hg. The resultant product is a homogeneous, semi-solid, extrudable paste product.

The dual component dentifrice composition of the present invention is packaged in a suitable dispensing container in which the components are maintained physically separated and from which the separated components may be dispensed synchronously. Such containers are known to the art. An example of such container is a dual compartmented dispensing container having collapsible sidewalls disclosed in U.S. Pat. Nos. 4,487,757 and 4,687,663 wherein the container body is formed from a collapsible plastic web and is provided with a partition within the container body defining separate compartments in which the physically separated components are stored and from which they are dispensed through a suitable dispensing outlet.

The following examples illustrate this invention further. All proportions and amounts therein and elsewhere in this specification are by weight unless otherwise indicated.

EXAMPLE I

A combined dentifrice composition of the present invention, designated 5 "Composition X", composed of a Component (A) and a Component (B) was prepared wherein the individual components contained the ingredients as set forth in the Table below.

|  | Dentifrice X (Wt. %) | |
|---|---|---|
| Ingredients | Component A | Component B |
| Deionized water | 3.000 | 24.940 |
| Glycerin (99.3%) | 25.000 | 22.000 |
| Sorbitol (70%) | 41.676 | — |
| Sodium lauryl sulfate | 1.200 | 1.200 |
| Dicalcium phosphate dihydrate (DCPD) | — | 49.520 |
| Titanium oxide | 0.500 | — |
| Saccharin | 0.200 | 0.200 |
| Sodium fluoride | 0.484* | — |
| Flavor | 0.890 | 0.890 |
| Polyethylene glycol 600 | 3.000 | — |
| Sodium carboxymethyl cellulose | 0.350 | 1.000 |
| Food Color FDC Blue #1 (1%) | 0.200 | — |
| Silicon Dioxide | 18.000 | — |
| Amorphous Silica | 5.500 | — |
| Tetrasodium pyrophosphate | — | 0.250 |
| Total | 100.000 | 100.000 |

*1100 ppm releasable $F^-$ in combined components.

The DCPD abrasive used in the preparation of Component A had a magnesium content of zero and a pyrophosphate content in the range of 0.1–0.4% by weight of the abrasive.

Fluoride Uptake Assay

An in vitro fluoride uptake method utilizing hydroxyapatite (HAP) disks was used to evaluate the performance of Components A and B when combined to form Dentifrice X. This in vitro fluoride uptake assay has been shown to correlate with intra-oral fluoride uptake in an intra-oral study in which enamel remineralization was also determined, i.e., the greater the fluoride uptake in the in vitro test, the greater the expected anticaries efficacy of the dentifrice.

In the in vitro fluoride uptake assay, commercially available 12 mm diameter sintered HAP disks were attached, three each, to a plastic microscope slide by placing a drop of impression compound wax between the disk and slide and pressing down firmly. The sides of each disk were then coated with this same wax to protect them from interacting with the acid solution. Each specimen was then prepared by cutting a circular shape using a dental handpiece to include an additional five millimeter diameter to the size of the disk. A small hole was drilled into a corner of each circular plastic microscope slide and four inches of plain dental floss was attached to each specimen for removal of the disks from the dentifrice treatment slurry at predetermined time intervals. Each specimen surface was abraded manually using 400 grit silicon carbide abrasive paper to ensure surface activation. After the surface was abraded, it was cleaned and polished on a grinding wheel using a diamond cloth wetted with a slurry of five micron alumina. Thereafter, the disks were placed in an ultrasonic bath for 10 minutes to remove any loose particles from the disk surfaces.

The ultrasonically cleaned disks were treated for five minutes using a slurry of 10 grams of Dentifrice X in thirty milliliters deionized water. After treatment, the disks were rinsed for fifteen seconds using deionized water.

One layer of hydroxyapatite was removed from each Dentifrice X slurry treated specimen by immersing the disk in five milliliters of 0.5 molar perchloric acid for four minutes in a shaker bath adjusted to about 100 pulses/min. The acid solutions were then buffered by the addition to the solution of 5 milliliters of TISAB (Total Ionic Solution Adjustment Buffer) which had been previously modified with NaOH to yield a final pH of 5.2.

A portion of the buffered solution was analyzed for fluoride ion amount with a fluoride specific ion electrode which was calibrated using standards prepared with the same buffer. The fluoride uptake for Dentifrice X is recorded in Table I below.

For purposes of comparison, the procedure of Example I was repeated except the DCPD abrasive used contained 0.5–0.8% by weight magnesium ion and 0.1 to 0.4% by weight pyrophosphate and was designated "Composition C". The fluoride uptake for Composition "C" is also recorded in Table 1.

For purposes of further comparison, a dual component dentifrice designated "Composition $C_1$", in which 24% by weight silica was substituted for the DCPD abrasive in Component 2 of Dentifrice X was also tested for fluoride ion uptake. The fluoride uptake for Composition $C_1$ is also recorded in Table 1.

TABLE 1.

TABLE 1

| Dentifrice | Fluoride ion Uptake μg/cm$^2$) | Standard Deviation |
|---|---|---|
| x | 3.72 | ± 0.36 |
| c | 3.16 | ± 0.08 |
| $c_1$ | 2.41 | ± 0.00 |

The fluoride deposition data recorded in Table I indicate that the dual component composition in which the magnesium ion content of the DCPD abrasive in the second component was less then 0.5% by weight i.e., no magnesium ion was present (Dentifrice X) unexpectedly deposited substantially more fluoride ion than comparative dual component compositions containing the same amount of fluoride ion in which the magnesium ion content of the DCPD abrasive in the second component was 0.5% by weight or greater (i.e., 0.5–0.08% by weight) (Composition C) or the dual component compositions contained only a silica abrasive and the same amount of fluoride ion (Composition $C_1$).

EXAMPLE II

The procedure of Example I was repeated with the exception that a DCPD abrasive containing 0.3% by weight magnesium ion was substituted for the DCPD abrasive used in Component 2 of Dentifrice X. These dentifrices were designated Dentifrice Y and Z.

For purposes of comparison, the procedure of Example II was repeated except the DCPD abrasive used contained 0.5–0.8% by weight magnesium ion. This comparative dentifrice was designated "Dentifrice $C_2$".

For purposes of further comparison, the procedure of Example II was repeated except that silica abrasive was substituted for the DCPD abrasive. This comparative dentifrice was designated "Dentifrice $C_3$".

The fluoride uptake on HAP disks of Dentifrice Y, Z, $C_2$ and $C_3$ is recorded in Table II below.

TABLE II

| Dentifrice | Fluoride Deposited on Cellulose Disk (macrograms/cm$^2$) | Standard Deviation |
|---|---|---|
| Y | 6.53 | ± 1.67 |
| Z | 6.67 | ± 0.86 |
| $C_2$ | 5.24 | ± 1.10 |
| $C_3$ | 4.53 | ± 1.10 |

The fluoride deposition data recorded in Table II indicate that the dual component compositions in which the magnesium ion content of DCPD abrasive in the second component of the present invention was less then 0.5% by weight (Dentifrice Y and Z) unexpectedly deposit substantially more fluoride than comparative dual component compositions containing the same amount of fluoride ion in which the magnesium ion content of DCPD abrasive in the second component was 0.5% by weight or greater (i.e. 0.5–0.8% by weight) (Dentifrice C2) or dual component compositions containing a silica abrasive and the same amount of fluoride ion (Dentifrice $C_3$).

What is claimed is:

1. A dual component dentifrice composition for the fluoridation of tooth structures the components being physically separated prior to extrusion in which a first component is a stable, semi-solid, extrudable dentifrice composition which is free of calcium ion and contains a fluoride releasable salt and the second component is a semi-solid, extrudable dentifrice composition containing a dicalcium phosphate abrasive having a magnesium ion content less than about 0.5% by weight based on the weight of the abrasive, the first and second dentifrice components having substantially equivalent viscosities to obtain synchronous extrusion of the components when dispensed for application to the teeth, the components when mixed upon application to teeth providing increased deposition of fluoride thereon.

2. The composition of claim 1 wherein the dicalcium phosphate abrasive is dicalcium phosphate dihydrate.

3. The composition of claim 1 wherein the fluoride releasable salt is NaF.

4. The composition of claim 1 wherein the magnesium ion concentration of the dicalcium phosphate abrasive is from 0 to 0.3% by weight.

5. The composition of claim 1 wherein the components are extrudable at a volume ratio of 0.9:1 to 1:0.9.

6. The composition of claim 1 wherein the components are extrudable at a volume ratio of 1:1.

7. A method for fluoridation of teeth which comprises preparing a dual component dentifrice composition in which a first component is a stable, semi-solid, extrudable dentifrice composition which is free of calcium ion and contains a fluoride releasable salt and the second component is a semi-solid, extrudable dentifrice composition containing a dicalcium phosphate abrasive having a magnesium ion content less than about 0.5% by weight based on the weight of the abrasive, the first and second dentifrice components being physically separated prior to extrusion and having substantially equivalent viscosities, synchronously extruding the components for application to the teeth and then mixing the components upon application to the teeth whereby enhanced deposition of fluoride on the teeth is obtained.

8. The method of claim 7 wherein the dicalcium phosphate abrasive is dicalcium phosphate dihydrate.

9. The method of claim 7 wherein the fluoride releasable salt is NaF.

10. The method of claim 7 wherein the magnesium ion concentration of the dicalcium phosphate abrasive is from 0 to 0.3% by weight.

11. the method of claim 7 wherein the components are extrudable at a volume ratio of 0.9:1 to 1:0.9.

12. The method of claim 7 wherein the components are extrudable at a volume ratio of 1:1.

13. The composition of claim 1 wherein the dicalcium phosphate abrasive is substantially free of magnesium ion content.

14. The method of claim 7 wherein the dicalcium phosphate abrasive is substantially free of magnesium ion content.

* * * * *